(12) United States Patent
Oishi et al.

(10) Patent No.: US 10,085,628 B2
(45) Date of Patent: Oct. 2, 2018

(54) ENDOSCOPE

(71) Applicant: FUJIFILM Corporation, Tokyo (JP)

(72) Inventors: Hiroyuki Oishi, Ashigarakami-gun (JP); Shozo Iyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 639 days.

(21) Appl. No.: 14/666,792

(22) Filed: Mar. 24, 2015

(65) Prior Publication Data
US 2015/0272430 A1 Oct. 1, 2015

(30) Foreign Application Priority Data

Mar. 25, 2014 (JP) ................................. 2014-061945

(51) Int. Cl.
*A61B 1/04* (2006.01)
*A61B 1/05* (2006.01)
(Continued)

(52) U.S. Cl.
CPC ............ *A61B 1/053* (2013.01); *A61B 1/0011* (2013.01); *A61B 1/00128* (2013.01);
(Continued)

(58) Field of Classification Search
CPC ................................. A61B 1/053; A61B 1/051
(Continued)

(56) References Cited

U.S. PATENT DOCUMENTS 5,746,695 A * 5/1998 Yasui ................. A61B 1/00091
600/121
6,447,445 B1 9/2002 Hirano
(Continued)

FOREIGN PATENT DOCUMENTS

JP 3-129915 U 12/1991
JP 8-136829 A 5/1996
(Continued)

OTHER PUBLICATIONS

Japanese Office Action dated Feb. 24, 2016, for corresponding Japanese Application No. 2014-061945 with the English translation is provided.

(Continued)

*Primary Examiner* — Alexandra L Newton
*Assistant Examiner* — Rynae Boler
(74) *Attorney, Agent, or Firm* — Birch, Stewart, Kolasch & Birch, LLP

(57) ABSTRACT

An endoscope includes: a tip portion main body provided at a tip portion of an insertion section; a camera unit attachment hole provided so as to penetrate the tip portion main body; a camera unit of which tip portion is fitted into a tip portion of the camera unit attachment hole; a locking member disposed at an outer peripheral surface of the camera unit so as to be movable in a direction that is orthogonal to the axial direction; a projection provided on either one of the locking member and the camera unit; a sliding portion provided on the other one of the locking member and the camera unit; and a locking biasing member configured to bias the locking member in the direction t orthogonal to the axial direction within the camera unit attachment hole and to push the locking member against the camera unit attachment hole.

25 Claims, 11 Drawing Sheets

(51) Int. Cl.
*A61B 1/00* (2006.01)
*H04N 5/225* (2006.01)

(52) U.S. Cl.
CPC ........... *A61B 1/051* (2013.01); *H04N 5/2257* (2013.01); *A61B 1/00096* (2013.01); *H04N 2005/2255* (2013.01)

(58) Field of Classification Search
USPC ............................. 600/112, 129, 172, 175
See application file for complete search history.

(56) References Cited

U.S. PATENT DOCUMENTS

| 6,605,035 B2* | 8/2003 | Ando | A61B 1/0008 600/127 |
| 2006/0173243 A1* | 8/2006 | Watanabe | A61B 1/0055 600/141 |
| 2016/0291312 A1* | 10/2016 | Satake | G02B 23/2484 |

FOREIGN PATENT DOCUMENTS

| JP | 2000-37343 A | 2/2000 |
| JP | 2001-83436 A | 3/2001 |
| JP | 2002-58635 A | 2/2002 |
| JP | 2007-330806 A | 12/2007 |

OTHER PUBLICATIONS

Extended European Search Report dated Jul. 22, 2015, for European Application No. 15160228.1.

\* cited by examiner

ENDOSCOPE

CROSS-REFERENCE TO RELATED APPLICATIONS

The present application claims priority under 35 U.S.C. § 119 to Japanese Patent Application No. 2014-061945, filed on Mar. 25, 2014. Each of the above application(s) is hereby expressly incorporated by reference, in its entirety, into the present application.

BACKGROUND OF THE INVENTION

1. Field of the Invention

The present invention relates to an endoscope having a camera unit.

2. Description of the Related Art

An endoscopes is equipped with an insertion section that is inserted into the inside of a subject's body, and a hand operating section that is connected to a base end of the insertion section. The insertion section is consisted of a tip portion, a bending portion, and a soft portion, which are provided consecutively from its tip. The bending portion has a structure in which a plurality of bending pieces are coupled together, and is bendingly operated by a bending operation wire provided inside bending pieces being pushed and pulled, and the orientation of a tip portion thereof is changed.

The tip portion of the insertion section is equipped with an observation window, an illumination window, a fluid jet nozzle, a treatment tool outlet, and the like. A camera unit for imaging the inside of a subject's body is provided in the back of the observation window. The illumination window allows illumination light to be radiated toward an imaging range of the camera unit therethrough. The fluid jet nozzle has a jet port at a tip thereof, and selectively jets, for example, liquids, such as cleaning water, or gases, such as air or carbon dioxide gas. A liquid jetted from the fluid jet nozzle flushes dirt on the observation window, and a gas blows away droplets remaining on the surface of the observation window. Various treatment tools are protruded from and retracted into a treatment tool outlet. Various kinds of treatment are performed with respect to affected parts by the treatment tools. Additionally, the treatment tool outlet also serves as a suction port, and when a treatment tool is not inserted through the treatment tool outlet, body fluids, filth, or the like is sucked from an affected part.

The camera unit has an optical system consisting of a plurality of optical components, such as a lens and a prism, and an imaging element, such as a charge-coupled device (CCD) that photoelectrically converts an optical image focused by the optical system into imaging signals. The imaging element is connected to a signal cable via a flexible substrate, a sub-substrate, and the like. Additionally, electronic components are mounted on the flexible substrate or the sub-substrate so as to drive the imaging element. Signals from the camera unit are sent to an image processor via the flexible substrate, the sub-substrate, and the signal cable. The image processor processes the signals, and thereby an image of a lesioned site and the like, is displayed on a monitor.

The signal cable that sends the signals from the camera unit to the image processor is constituted by a composite multi-core cable. Since this signal cable is inserted through an insertion section over its entire length, the signal cable is strongly pushed and pulled whenever the insertion section is looped or bent. For this reason, the camera unit is firmly attached to the tip portion, using various fixing means. The fixing means include: a fixing screw or an adhesive (refer to FIG. 5 of JP1996-136829 (JP-H08-136829A), FIG. 2 of JP2000-37343A, and FIG. 22 of JP2007-330806A); the fitting between a projection and a recessed groove (refer to FIG. 6 of JP2001-83436A), fixing with pressure using a fixing member (refer to FIG. 10 of JP2002-58635A).

For example, as in endoscopes described in JP1996-136829 (JP-H08-136829A) and JP2000-37343A, a camera unit is attached to an attachment hole by attaching a fixing screw to a fixing screw hole provided in a tip portion after a lens frame of the camera unit is inserted into a camera unit attachment hole provided in the tip portion.

In an endoscope described in JP2007-330806A, a V-shaped groove is formed in an outer peripheral portion of a lens frame of a camera unit, and a fixing screw hole is formed in an attachment hole of the lens frame of a tip portion. After the lens frame of the camera unit is inserted into the attachment hole, the tip of the fixing screw is pressed against a tip-side inclination surface of the V-shaped groove by screwing the fixing screw to the fixing screw hole. Accordingly, the camera unit is screw-fastened and fixed in a state where the camera unit is pushed against the attachment hole to the tip side.

In an endoscope described in JP2001-83436A, a tip portion is constituted by a holding portion and a cover portion, and a recessed groove is formed in an outer peripheral surface of the holding portion. A camera unit is inserted into the recessed groove. Additionally, a positioning recess is formed in the recessed groove, and a projection is provided on the camera unit. The camera unit is fixed to the tip portion by the fitting between the projection and the positioning recess.

In an endoscope described in JP2002-58635A, a fixing member is screw-fastened and fixed to a tip portion, in a state where a camera unit is pressed against and fixed to a housing hole of the tip portion, using the fixing member.

SUMMARY OF THE INVENTION

When the lens frame of the camera unit is fixed using the fixing screw as in JP1996-136829 (JP-H08-136829A), JP2000-37343A, and JP2007-330806A, the lens frame may be deformed by the tip of the screw. If the lens frame is deformed, when the movable lens is arranged within the lens frame, the movable lens is caught in the deformed portion, for example, when power is varied, and a poor variable power operation occurs in which a captured image blurs or an image is skipped. Additionally, even when there is no movable lens, it is not preferable to deform the lens frame.

As in JP2001-83436A, since no fixing screw is used in a method of forming a positioning groove in the recessed groove that is the housing portion of the camera unit, fitting the projection provided on the camera unit into the positioning groove, and fixing the camera unit to the tip portion, the lens frame is not deformed by the tip of the fixing screw. However, since the attachment position of the camera unit to the tip portion is fixed by a positional relationship between the positioning groove and the projection, a new problem occurs in that the axial position of the camera unit is not changed within the tip portion.

As in JP2002-58635A, when the camera unit is fixed to the tip portion via the fixing member, the lens frame of the camera unit is not deformed by the tip of the screw. However, since a structure in which the thick fixing member is fastened with a screw is provided, the thick fixing member or the thick fixing screw is required, and configuration becomes complicated. Additionally, in a situation where it is desired to make the diameter of the insertion section small from a request for alleviating a burden to a subject, there is interference or the like with other built-in things, and effective arrangement that is effective in making the diameter of the fixing member and the fixing screw small is difficult.

The invention has been made in view of the above problems, and an object thereof is to provide an endoscope that can eliminate deformation of a camera unit caused by a fixing screw and can finely adjust the axial attachment position of the camera unit when the camera unit is fixed to a tip portion and that can also cope with a request for small diameter.

An endoscope of the invention includes a tip portion main body, a camera unit, a locking member, and a locking biasing member. The tip portion main body is provided at a tip portion of an insertion section to be inserted into the inside of a body and has a camera unit attachment hole. The camera unit attachment hole is provided so as to penetrate the tip portion main body in an axial direction of the insertion section. The camera unit has a tip portion fitted into a tip portion of the camera unit attachment hole, in a state where the camera unit is inserted into the camera unit attachment hole. The locking member is disposed at an outer peripheral surface of the camera unit so as to be movable in a direction orthogonal to the axial direction, in a state where the locking member is inserted into a base end side of the camera unit attachment hole. A projection is provided on either one of the locking member and the camera unit, and a sliding portion is provided on the other one of the locking member and the camera unit. The sliding portion regulates movement of the projection in the axial direction, and enables the projection to slide in the direction orthogonal to the axial direction. The locking biasing member biases the locking member in the direction orthogonal to the axial direction within the camera unit attachment hole and pushes the locking member against the camera unit attachment hole, thereby fixing the locking member, in a state where the camera unit is inserted into the camera unit attachment hole.

The camera unit may include a housing having a lens holding barrel at a tip thereof. The camera unit attachment hole may include a lens holding barrel fitting hole to which the lens holding barrel and be fitted; a housing fitting hole to which the housing can be fitted, the housing being provided continuously with a base end side of the lens holding barrel fitting hole; and a locking member housing groove in which the locking member can be housed, the locking member housing groove being provided continuously with the housing fitting hole.

The camera unit may include a prism and a prism holding frame that holds the prism. The prism and the prism holding frame may be provided continuously with the lens holding barrel. The camera unit may further include an attachment plate portion that is fixed to the prism holding frame and have the projection or the sliding portion.

The camera unit may include a reinforcing member of which base end is fixed to a signal cable and of which tip is fixed to the prism holding frame. The reinforcing member may protect built-in elements between the prism holding frame and the signal cable. The attachment plate portion may be formed integrally with the reinforcing member.

The projection may be provided on the attachment plate portion. The sliding portion may be a groove or an elongated hole, which is long in the direction orthogonal to the axial direction. The projection may be provided in the locking member.

The locking member may be a locking plate that is bent at both side edges thereof, and the locking member housing groove may have rail portions that guide both of the side edges in the axial direction.

The regions of the camera unit that face both of the side edges may have inclination surfaces, and the rail portions may be formed in proximity to the inclination surfaces.

The locking biasing member may be a fixing screw that is inserted from an outer peripheral surface of the tip portion main body and thereby push the locking member against the camera unit attachment hole. The locking biasing member may be a wedge member that is inserted from an outer peripheral surface of the tip portion main body and thereby push the locking member against the camera unit attachment hole.

The tip portion main body may include a locking member exposure opening from which exposed is a side edge of the locking member that is pushed against a side wall within the camera unit attachment hole by being biased by the locking biasing member.

According to the invention, the camera unit can be firmly attached to the tip portion main body, eliminating deformation of the camera unit caused by fastening the fixing screw, and the attachment position of the camera unit to the tip portion main body can be finely adjusted. Additionally, a compact device configuration can be achieved, and the diameter of the insertion section can be made small.

DESCRIPTION OF THE PREFERRED EMBODIMENTS

First Embodiment

Figure 1:
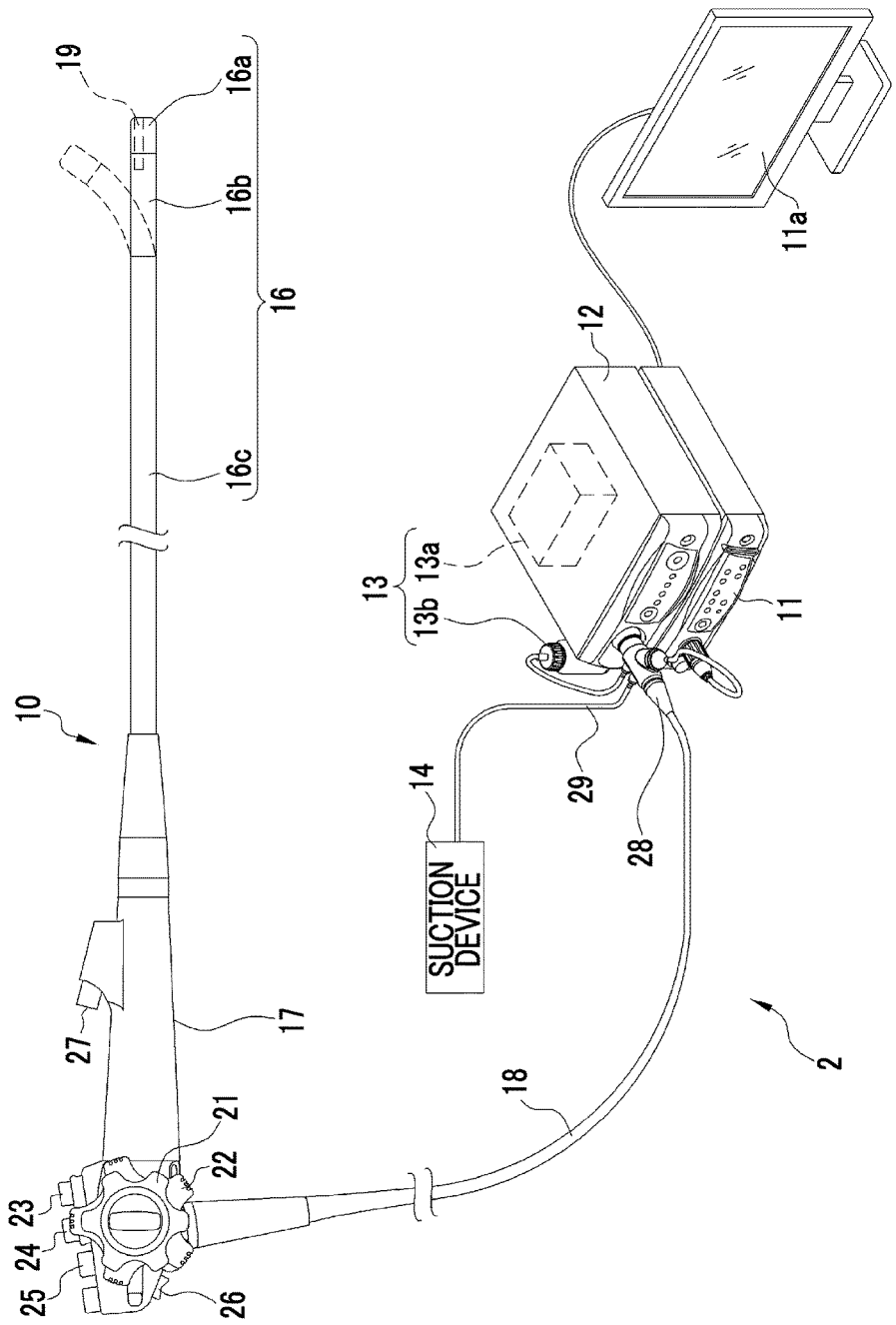
FIG. 1 is a perspective view illustrating an electronic endoscope system of the invention.

As illustrated in FIG. 1, an endoscope system 2 is equipped with an electronic endoscope 10, a processor device 11, a light source device 12, a gas/liquid feed device 13, and a suction device 14. The gas/liquid feed device 13 has a well-known gas feed device (pump or the like) 13a that is built into the light source device 12 and performs feeding of gas, and a liquid tank 13b that is provided outside the light source device 12 and stores a liquid. The electronic endoscope 10 has a flexible insertion section 16 to be inserted into the inside of the body, a hand operating section 17 provided continuously with a base end portion of the insertion section 16, and a universal cord 18 connected to the processor device 11 and the light source device 12.

The insertion section 16 has a tip portion 16a, a bending portion 16b, and a soft portion 16c sequentially from its tip. A camera unit 19 for imaging the inside of a subject's body is built into the tip portion 16a. The bending portion 16b is provided continuously with a base end of the tip portion 16a, and is configured in a bendable manner. The soft portion 16c is provided continuously with a base end of the bending portion 16b, and has flexibility.

The hand operating section 17 is provided with a treatment tool inlet 27 in addition to various operating members, such as bending operation knobs 21 and 22, a gas/liquid feed button 23, a suction button 24, a release button 25, and a seesaw switch 26 for zoom operation. A connector 28 is attached to the other end of the universal cord 18. The connector 28 is a complex type connector, and the processor device 11, the light source device 12, and the gas/liquid feed device 13 are connected to the connector, respectively. The suction device 14 is connected to the connector 28 via a coupling tube 29.

The processor device 11 is electrically connected to the light source device 12, and generally controls the operation of the endoscope system 2. The processor device 11 supplies electric power to the electronic endoscope 10 via a signal cable 68 (refer to FIG. 2) inserted into the universal cord 18 and the insertion section 16, and controls the driving of the camera unit 19. Additionally, the processor device 11 receives imaging signals output from the camera unit 19 via the signal cable 68, and performs various kinds of image processing to generate image data. The processor device 11 displays an observation image on a monitor 11a on the basis of this image data.

When the bending operation knobs 21 and 22 of the hand operating section 17 are operated, a wire inserted into the insertion section 16 is pushed or pulled, and thereby the bending portion 16b is bent in vertical and horizontal directions. Accordingly, the tip portion 16a is directed to a desired direction within the subject's body. If the gas/liquid feed button 23 is operated, a liquid or a gas is selectively jetted from the fluid jet nozzle 43, and cleaning of an observation window 40, illumination windows 41 and 42 (refer to FIG. 3), or the like is performed. If the suction button 24 is operated, suction is performed from a treatment tool outlet 35 (refer to FIG. 3), and body fluids, dirt, droplets that have remained on a tip surface, or the like is sucked. If the release button 25 is operated, an image captured from the observation window 40 is taken into a memory, and can be displayed or printed as a still image afterward.

Figure 2:
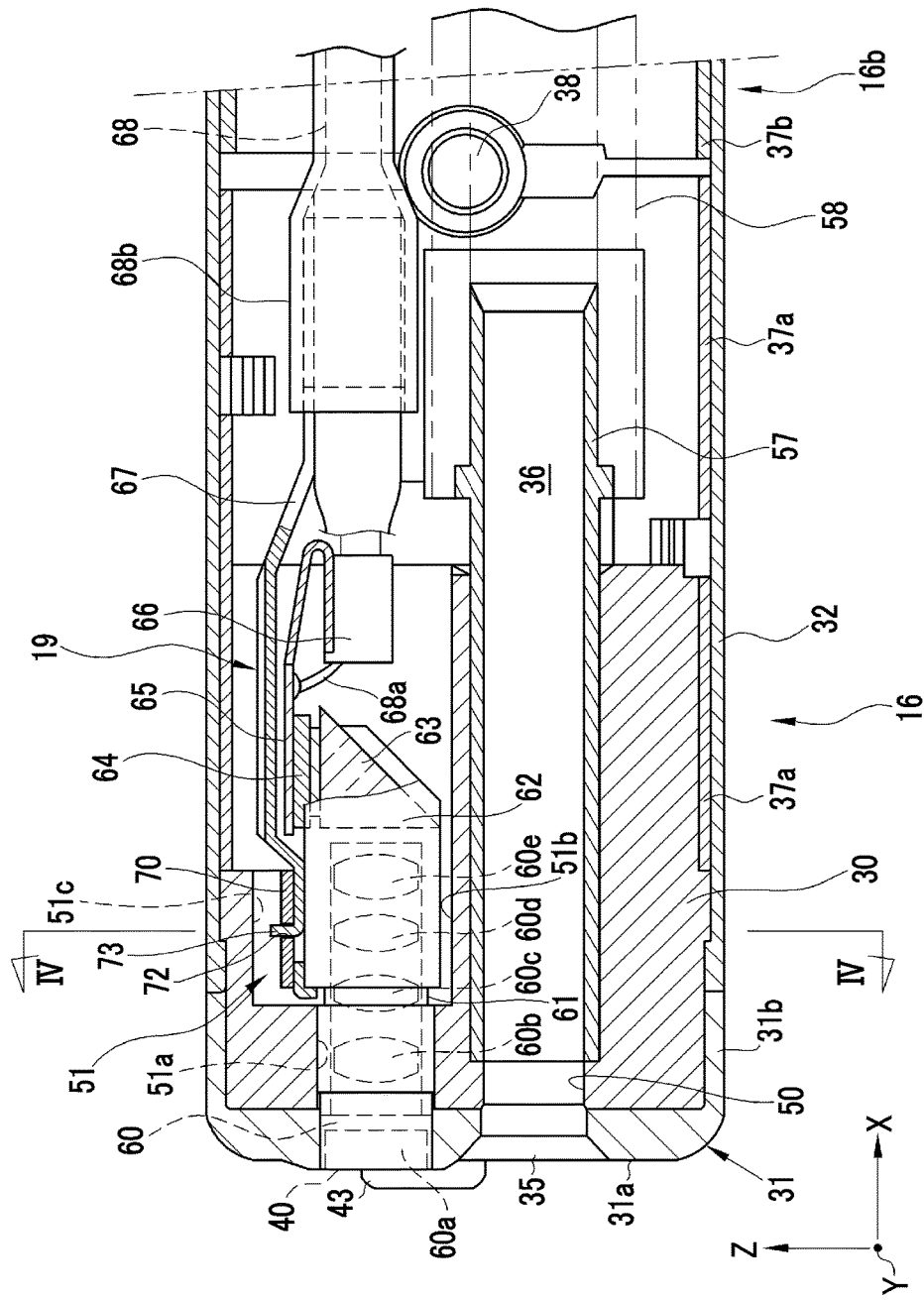
FIG. 2 is a cross-sectional view taken along line II-II of FIG. 4 illustrating a tip portion.

As illustrated in FIG. 2, the tip portion 16a is equipped with a substantially columnar tip portion main body 30, a tip cap 31 that is attached so as to cover the tip portion main body 30, and a covering tube 32 made of rubber. A tip bending piece 37a is coupled to a base-end-side outer peripheral surface of the tip portion main body 30. The bending portion 16b is configured by coupling the tip bending pieces 37a, a plurality of intermediate bending pieces 37b, and a base end bending piece (not illustrated) together using a coupling pin 38, and is bendable in vertical and horizontal directions. The tip cap 31 has a tip plate portion 31a that covers a tip surface of the tip portion main body 30, and a cylinder portion 31b that covers a tip-side outer peripheral surface of the tip portion main body 30. The covering tube 32 is a shell for the tip portion main body 30 and the bending portion 16b, and extends from a tip of the soft portion 16c (refer to FIG. 1) to the tip portion main body 30. In addition, the bending portion 16b is illustrated in a simplified manner, and a netlike braid obtained by braiding element wires made of metal or a covering tube made of rubber is omitted.

Figure 3:
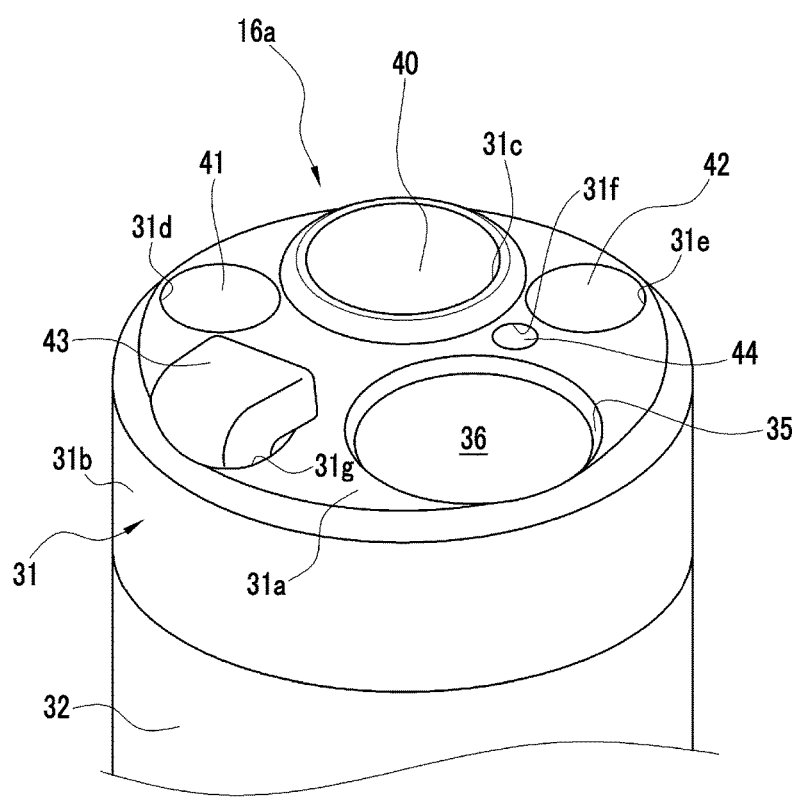
FIG. 3 is a perspective view illustrating the tip portion.

As illustrated in FIG. 3, the tip plate portion 31a of the tip cap 31 is formed with the treatment tool outlet 35 and circular openings 31c to 31g. A treatment tool insertion conduit 36 communicates with the treatment tool outlet 35. An observation window 40, illumination windows 41 and 42, and a water jet port (WJ jet port) 44, which are attached to the tip portion main body 30, are exposed to the openings 31c to 31f. Additionally, a fluid jet nozzle 43 is attached to the opening 31g.

The illumination windows 41 and 42 also serve as irradiation lenses, and allow a region to be observed within a living body to be irradiated with the illumination light from the light source device 12 therethrough. Emission ends of light guides 45 and 46 (refer to FIG. 4) face the illumination windows 41 and 42. The light guides 45 and 46 are formed by bundling a number of optical fibers. As illustrated in FIG. 1, the light guides 45 and 46 guide the illumination light from the light source device 12 to the illumination windows 41 and 42 through the inside of the insertion section 16, the hand operating section 17, the universal cord 18, and the connector 28. In addition, the light guided from the light source device 12 may be, for example, excitation light, such as laser light. In this case, a system is preferable which guides the excitation light from the light source device 12 with a single-line optical fiber, makes a fluorescent body disposed at the tip portion 16a emit light, and radiates illumination light.

Figure 4:
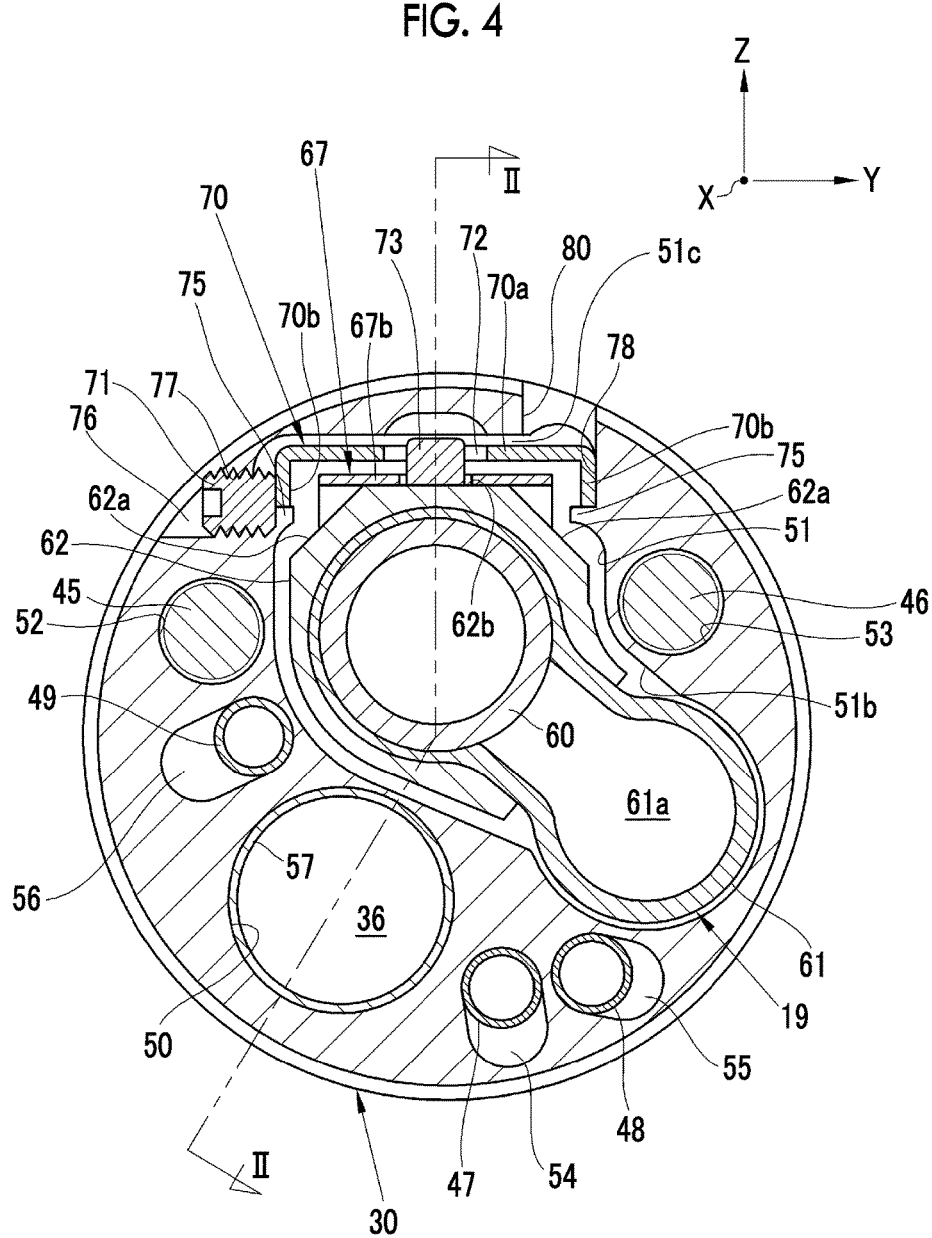
FIG. 4 is a cross-sectional view taken along line IV-IV of FIG. 2 illustrating an attachment state of a camera unit to a tip portion main body.

As illustrated in FIG. 4, the tip portion main body 30 is formed with a treatment tool insertion conduit attachment hole 50 penetrating parallel to an axial direction X of the insertion section 16, a camera unit attachment hole 51, light guide insertion holes 52 and 53, a gas feed tube insertion hole 54, a liquid feed tube insertion hole 55, and a WJ tube attachment hole 56, a fluid jet nozzle attachment hole (not illustrated), and the like are formed. An attachment cylinder 57 is disposed in the treatment tool insertion conduit attachment hole 50. The camera unit 19 is disposed in the camera unit attachment hole 51. The light guides 45 and 46 are disposed in the light guide insertion holes 52 and 53, respectively. A gas feed tube 47 is disposed in the gas feed tube insertion hole 54. A liquid feed tube 48 is disposed in the liquid feed tube insertion hole 55. The WJ tube 49 is disposed in the WJ tube attachment hole 56. In addition, on the basis of FIG. 4, description will be made with the axial direction of the insertion section 16 being defined as an X-axis, a horizontal axis orthogonal to the X-axis being defined as a Y-axis, and a vertical axis orthogonal to the X-axis being defined as a Z-axis, and the following respective axial directions being described as an X direction, a Y direction, and a Z direction.

As illustrated in FIG. 2, the treatment tool insertion conduit attachment hole 50 is formed at a position corresponding to the treatment tool outlet 35, and constitutes a portion of the treatment tool insertion conduit 36. The attachment cylinder 57 is fitted and anchored to the treatment tool insertion conduit attachment hole 50. One end of a treatment tool tube 58 is connected to a base end side of the attachment cylinder 57, and the other end of the treatment tool tube 58 is connected to the treatment tool inlet 27 (refer to FIG. 1). The treatment tool insertion conduit 36 is constituted by the treatment tool insertion conduit attachment hole 50, the attachment cylinder 57, and the treatment tool tube 58.

As illustrated in FIG. 1, a plug (not illustrated) is attached to the treatment tool inlet 27, and the treatment tool inlet is plugged up. When a treatment tool is inserted, a valve of the plug is opened by the insertion of the treatment tool, and as illustrated in FIG. 2, the treatment tool is protruded from and retracted into the treatment tool outlet 35 through the treatment tool insertion conduit 36. As the treatment tool, for example, an injection needle, a high-frequency knife, or the like is used. Additionally, a suction conduit (not illustrated) branches from the treatment tool insertion conduit 36, and the suction conduit is connected to the suction button 24 of the hand operating section 17.

The camera unit attachment hole 51 has a lens holding barrel fitting hole 51a, a housing fitting hole 51b, and a locking plate housing groove (locking member housing groove) 51c. A lens holding barrel 60 of the camera unit 19 is fitted to the lens holding barrel fitting hole 51a. The housing fitting hole 51b has a housing 61 of the camera unit 19 fitted thereto, and is provided continuously on a base end side of the lens holding barrel fitting hole 51a. The locking plate housing groove 51c has the locking plate (locking member) 70 housed therein and is formed continuously with the housing fitting hole 51b.

Figure 5:
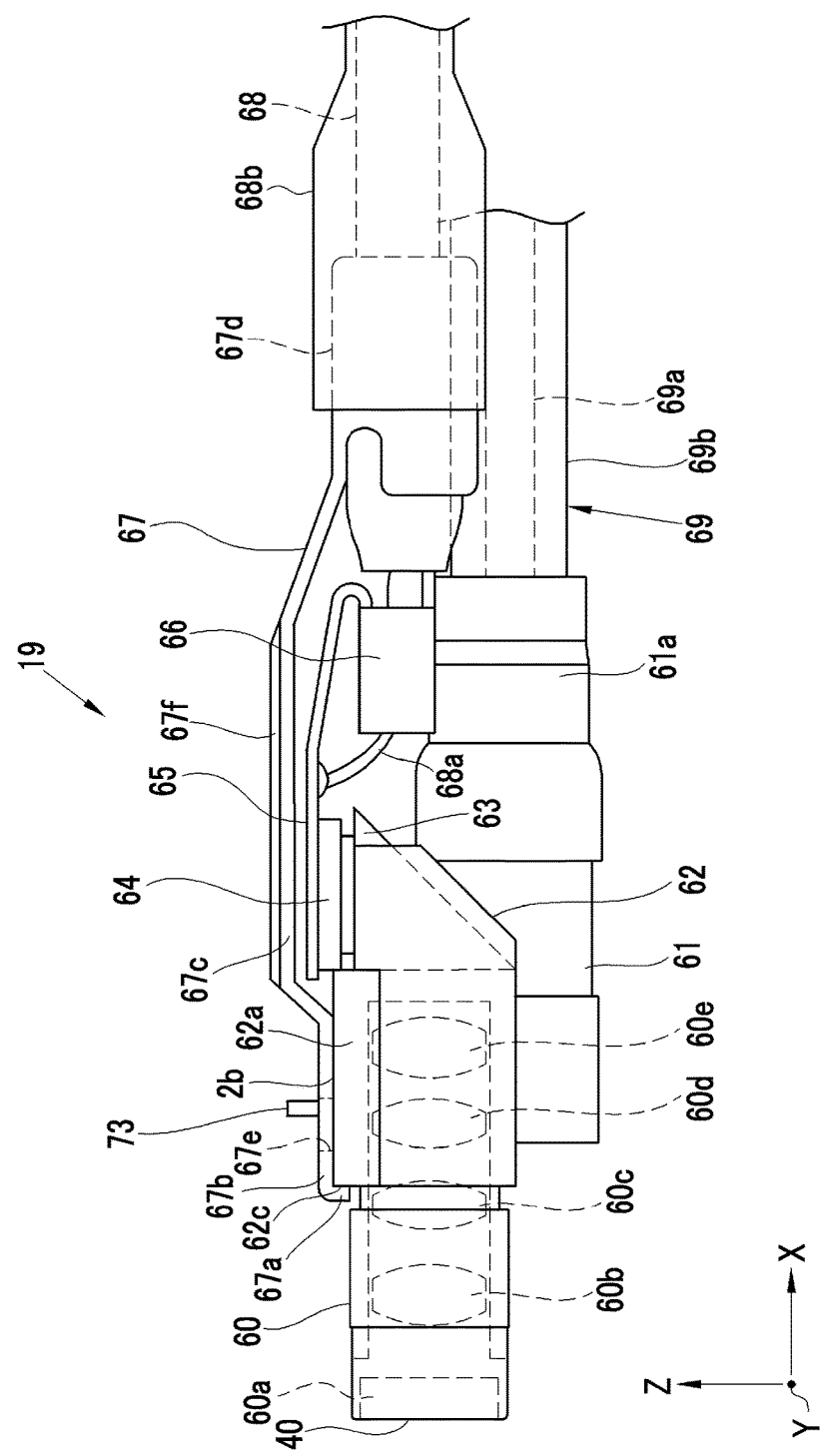
FIG. 5 is a side view of the camera unit.
Figure 6:
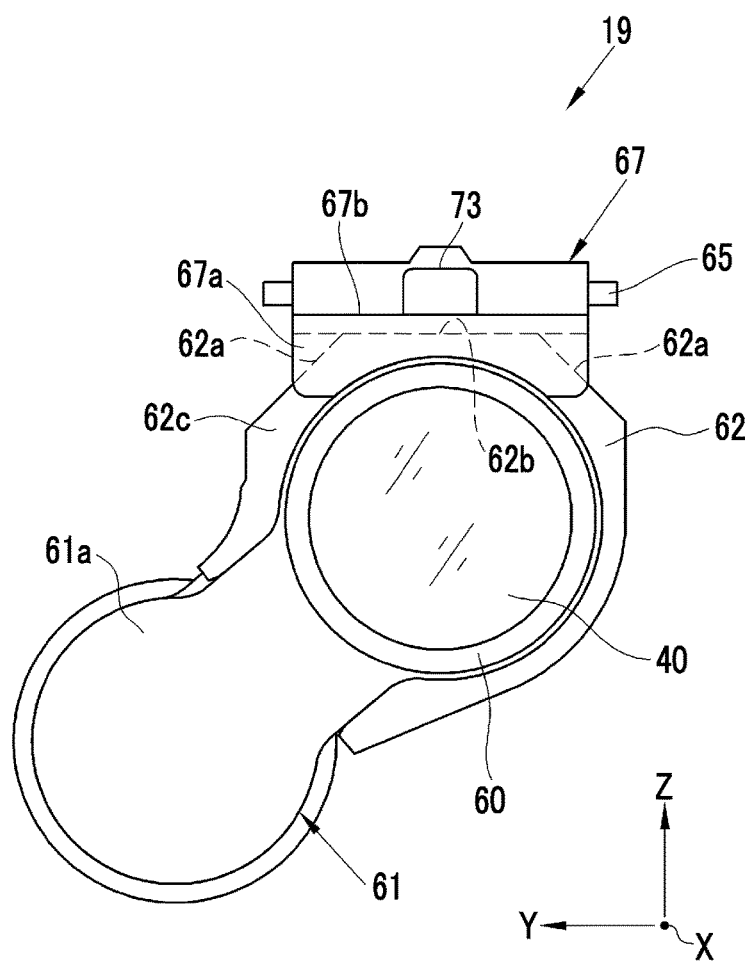
FIG. 6 is a front view of the camera unit.
Figure 7:
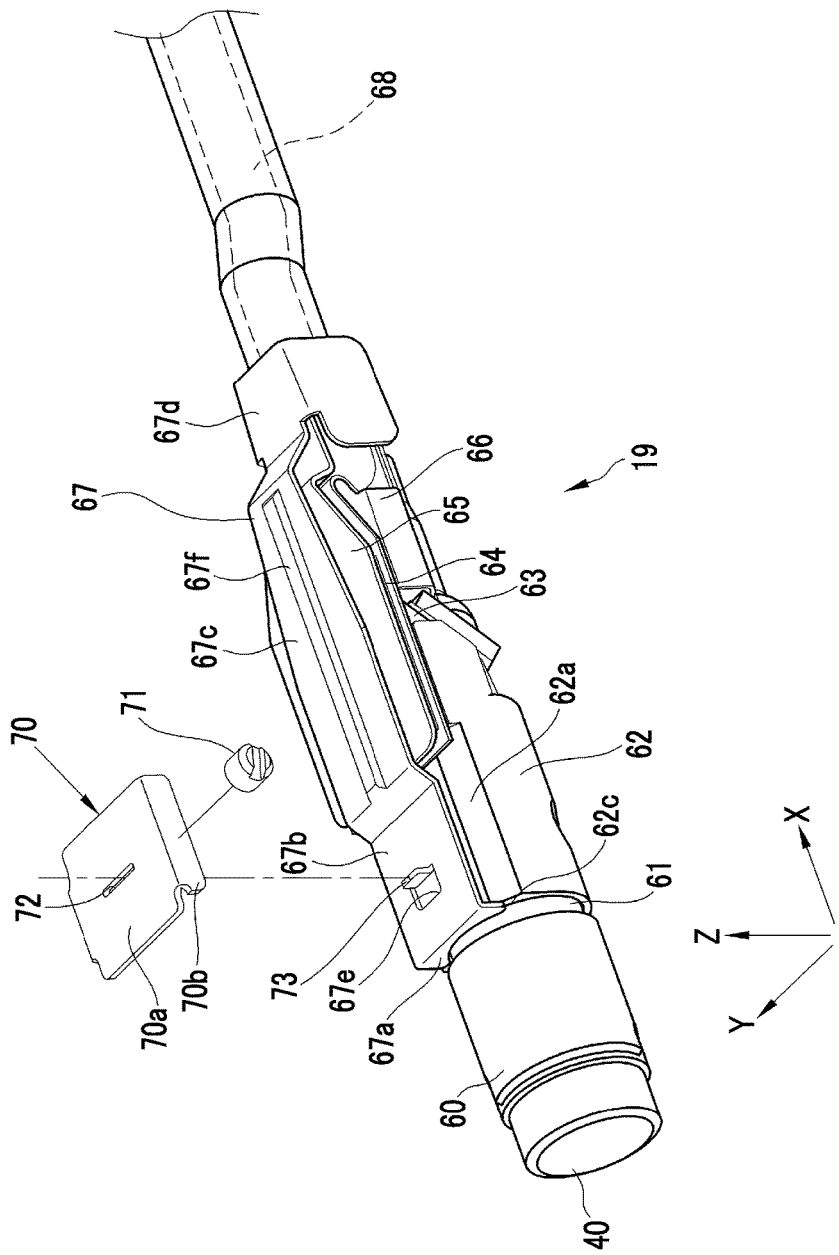
FIG. 7 is a perspective view of the camera unit.

As illustrated in FIGS. 5 to 7, the camera unit 19 has the housing 61 having the lens holding barrel 60, a prism holding frame 62, a prism 63, an imaging element 64, a main substrate 65, a sub substrate 66, a reinforcing plate (reinforcing member) 67, a signal cable 68, and a wire cable 69 sequentially from its tip.

Figure 8:
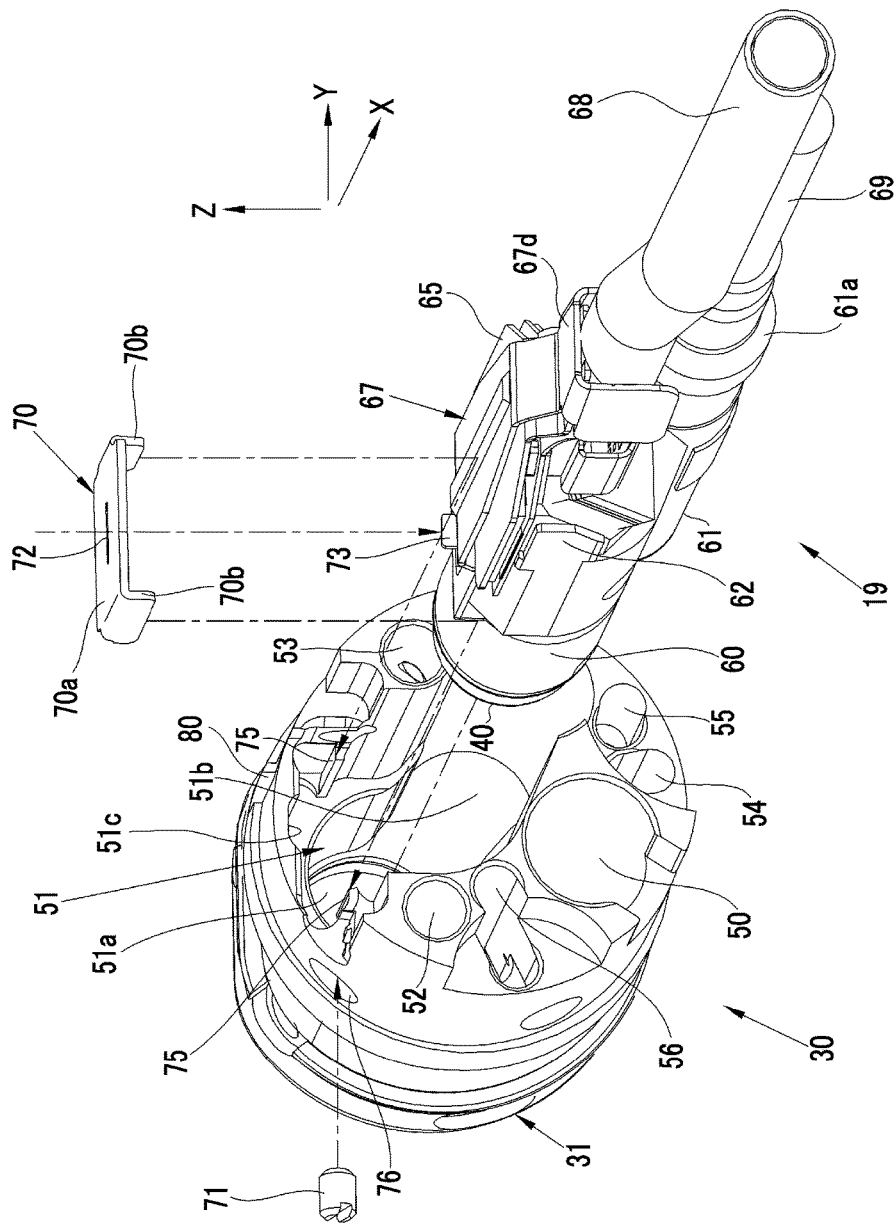
FIG. 8 is an exploded perspective view illustrating attachment of the camera unit to the tip portion main body.

As illustrated in FIG. 6, the housing 61 is formed by coupling two cylindrical bodies side by side in a direction orthogonal to a cylinder core and is formed in the shape of FIG. 8 in as seen from the front. One cylindrical body is constituted as the lens holding barrel 60, and the other cylindrical body is constituted as a lens drive unit 61a.

As illustrated in FIG. 5, the lens holding barrel 60 has a plurality of lenses 60a to 60e. In the present embodiment, the lenses 60a to 60c, and the lens 60e are fixed in an optical axis direction (X direction), and the lens 60d is a movable lens that is movable in the X direction. As the lens 60d moves in the X direction, this lens is zoomable. The lens 60a on the tip side also serves as a cover glass, and constitutes the observation window 40. In addition, a cover glass may be used instead of the tip lens 60a.

The lens drive unit 61a has a cam shaft and a cam-shaft engagement frame (not illustrated), and the cam-shaft engagement frame is coupled to and integrated with the movable lens 60d. A wire 69a of the wire cable 69 is coupled to the cam shaft. The wire 69a is inserted into the wire tube 69b and is rotated by a motor (not illustrated) disposed within the hand operating section 17 (refer to FIG. 1). The motor is rotationally driven by the operation of the seesaw switch 26 (refer to FIG. 1) of the hand operating section 17. The cam shaft is rotated via the wire 69a by the rotation of the motor, and the movable lens 60d is moved to the optical axis direction (X direction) by the rotation of the cam shaft, thereby performing zooming. In addition, one movable lens 60d may be provided or two or more movable lenses may be provided.

As illustrated in FIGS. 6 and 7, the prism holding frame 62 covers the lens holding barrel 60 and is provided integrally with the housing 61. The prism holding frame 62 has inclination surfaces 62a, which are obtained by chamfering upper corners, on both sides of an upper surface 62b.

As illustrated in FIG. 2, the optical axis of an imaging optical system including the lens holding barrel 60 and the prism 63 is bent at 90° by the prism 63. The imaging element 64 is arranged so that an emission surface, through which image light is emitted from the prism 63, and an imaging surface face each other. The imaging element 64 consists of, for example, an interline transfer type CCD, and photoelectrically converts an optical image focused by the imaging optical system into imaging signals. In addition, the imaging element 64 may be complementary metal oxide semiconductor (CMOS) or other devices, without being limited to the CCD.

The imaging element 64 is attached to the flexible main substrate 65. The main substrate 65 and the sub substrate 66 are connected together via a flexible wiring pattern, and components that could not be attached to the main substrate 65 are attached to the sub substrate 66. A drive circuit that drives the imaging element 64 is constituted of the main substrate 65 and the sub substrate 66. The sub substrate 66 is not fixed to, particularly, the prism holding frame 62. However, the sub substrate may be attached by temporary attachment if necessary, or may be attached by pinching the side edge of the sub substrate with the prism holding frame 62. In addition, the sub substrate 66 may be anchored to the reinforcing plate 67 or the like by being filled with sealing resin (not illustrated). Additionally, the sub substrate 66 may be omitted and only the main substrate 65 may be used.

As illustrated in FIG. 7, the reinforcing plate 67 is formed by bending a metal plate. The reinforcing plate 67 has a locking claw 67a, an attachment plate portion 67b, a reinforcing plate main body 67c, and a signal cable coupling portion 67d from the tip toward the base end. The locking claw 67a is formed at a tip of the attachment plate portion 67b, and is locked to a tip surface 62c of the prism holding frame 62. As illustrated in FIG. 6, the attachment plate portion 67b is bonded to the upper surface 62b of the prism holding frame 62 with an adhesive, and the prism holding frame 62 and the reinforcing plate 67 are integrated with each other.

As illustrated in FIG. 7, a central portion of the attachment plate portion 67b has a U-shaped cutout 67e. A central piece, which is left after being cut out in a U-shape by the cutout 67e, is bent at 90°, and serves as a projection 73 that is long in the width direction (Y direction) of the attachment plate portion 67b.

The reinforcing plate main body 67c is formed such that a reinforcing rib 67f extending in the optical axis direction (X direction) protrudes, and protects built-in elements, such as the prism 63, the imaging element 64, the main substrate 65, and the sub substrate 66, as illustrated in FIG. 5. The signal cable coupling portion 67d is formed so as to have a U-shaped cross-section by bending both side edges thereof inward at 90° (refer to FIG. 7), and is attached so as to cover the shell of the tip of the signal cable 68. By using the reinforcing plate 67 obtained by bending a metal plate in this way, the width of the camera unit 19 can be suppressed to be low and can be compactly put together. In addition, reference numeral 68b represents a protective tube that protects the signal cable 68. The element wire 68a of the signal cable 68 is connected to the main substrate 65 and the sub substrate 66.

As illustrated in FIG. 7, since the locking claw 67a of the reinforcing plate 67 is locked to the tip surface 62c of the prism holding frame 62, the reinforcing plate 67 is firmly coupled to the prism holding frame 62. For this reason, when the bending portion 16b (refer to FIG. 1) is bent, even if the signal cable 68 may be pulled according to this bending, the pulling force from the signal cable 68 acts only on the reinforcing plate 67 and the prism holding frame 62 and does not act on the element wire 68a. Therefore, disconnection of the element wire 68a, solder peeling, or the like does not occur.

As illustrated in FIG. 8, the camera unit 19 is inserted into the camera unit attachment hole 51 of the tip portion main body 30, and is fixed to the tip portion main body 30 by a locking plate 70 and a fixing screw (locking biasing member) 71.

The locking plate 70 is formed so as to have a U-shaped cross-section by bending both side edges of a metallic plate main body 70a at 90° to form a vertical plate portion 70b. An elongated hole 72 serving as a sliding portion is formed in the plate main body 70a to be long in the Y direction orthogonal to the optical axis. In addition, the term "orthogonal" also includes, for example, substantially orthogonal, in addition to orthogonal to the optical axis or an axial center.

Figure 9:
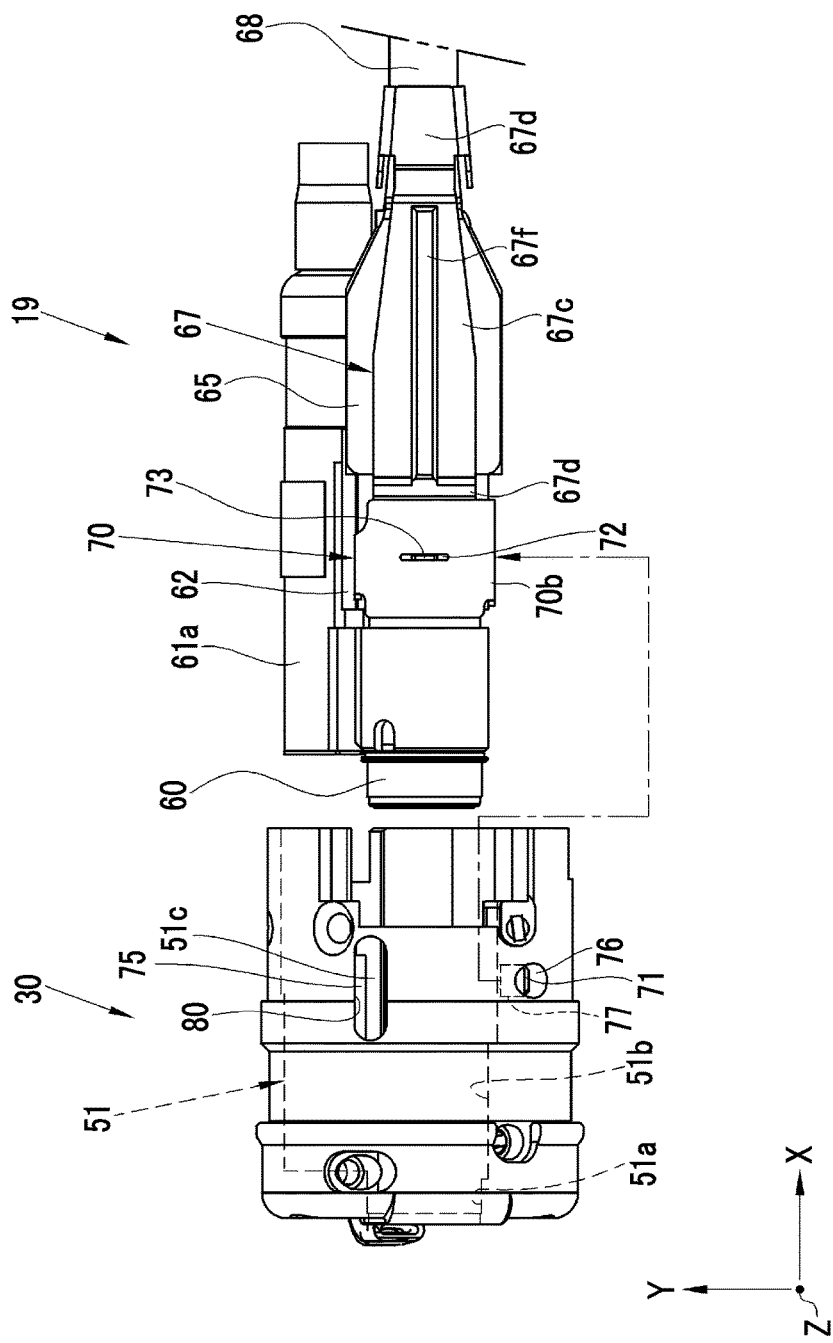
FIG. 9 is a plan view illustrating the attachment of the camera unit to the tip portion main body.

By inserting the projection 73 of the reinforcing plate 67 into the elongated hole 72, as illustrated in FIG. 9, the locking plate 70 is put on the attachment plate portion 67b. A width that is the X-direction length of the elongated hole 72 is approximately equal to the thickness of the projection 73, and movement of the projection 73 in the X direction is regulated within the elongated hole 72 in a state where the projection 73 is slidable in the Y direction. Additionally, the length of the projection 73 in the Y direction is shorter than the length of the elongated hole 72 of the locking plate 70, and the locking plate 70 is movable within a range of a gap between the elongated hole 72 and the projection 73.

As illustrated in FIG. 8, the lens holding barrel fitting hole 51a has the same circular cross-sectional shape as the lens holding barrel 60, and has the lens holding barrel 60 fitted thereto. The housing fitting hole 51b has substantially the same cross-sectional shape as the housing 61 and the prism holding frame 62, and has the housing 61 and the prism holding frame 62 fitted thereto. An upper portion of the housing fitting hole 51b is formed with the locking plate housing groove 51c.

As illustrated in FIG. 4, a pair of rail portions 75 are formed between the locking plate housing groove 51c and the housing fitting hole 51b so as to protrude toward the inside. Both side edges of the upper surface 62b of the prism holding frame 62 are chamfered to form the inclination surfaces 62a. The rail portions 75 are formed in cutout spaces formed by the inclination surfaces 62a so as to protrude therefrom. Accordingly, the rail portions 75 enter the cutout spaces, the rail portions 75 face the inclination surfaces 62a, and both of the rail portions and the inclination surfaces approach each other. Therefore, since the rail portion 75 can be formed by effectively using the cutout spaces, the attachment plate portion 67b and the locking plate 70 can be compactly put together, and the diameter of the tip portion 16a can be made smaller.

The vertical plate portion 70b of the locking plate 70 is placed on the rail portions 75, and the locking plate 70 is held within the locking plate housing groove 51c so as to be movable in the X direction via the rail portions 75. The groove width of the locking plate housing groove 51c is formed so as to be slightly greater than the width of the locking plate 70. For this reason, the movement of the locking plate 70 in the Y direction is allowed by the margin of the groove width.

A fixing screw insertion hole 76 and a screw hole 77 are formed at a position corresponding to the locking plate housing groove 51c in an outer peripheral surface of the tip portion main body 30. As illustrated in FIG. 9, the fixing screw insertion hole 76 and the screw hole 77 (refer to FIG. 4) are formed in the outer peripheral surface of the tip portion main body 30 so that the fixing screw 71 is located in the middle of the vertical plate portion 70b of the locking plate 70 in the X direction, in a state where the camera unit 19 is put into the camera unit attachment hole 51.

As illustrated in FIG. 4, the fixing screw 71 is inserted into the fixing screw insertion hole 76 and is screwed to the screw hole 77. If the fixing screw 71 is rotated, the locking plate 70 is pushed in the Y direction by the entry of the fixing screw 71. Then, the locking plate 70 is fixed within the locking plate housing groove 51c by pushing one vertical plate portion 70b of the locking plate 70 against a side wall 78 of the locking plate housing groove 51c.

A locking plate exposure opening (locking member exposure opening) 80 is formed above the rail portions 75 opposite to a side where the fixing screw 71 of the locking plate housing groove 51c is attached. As an adhesive (not illustrated) is injected from the locking plate exposure opening 80, the locking plate 70 and the locking plate housing groove 51c can be more firmly fastened. Additionally, when the camera unit 19 is detached from the tip portion main body 30 in the case of maintenance, a minus driver or the like is inserted between the side wall 78 of the locking plate housing groove 51c and the vertical plate portion 70b of the locking plate 70 to form a gap therebetween, in a state where the fixing screw 71 is loosened and the pushing and fixing of the locking plate 70 is released. The formation of this gap enables the fastening between the locking plate 70 and the locking plate housing groove 51c using the adhesive to be released.

As illustrated in FIG. 8, when the camera unit 19 is attached to the tip portion main body 30, the lens holding barrel 60 of the tip of the camera unit 19 is inserted into the lens holding barrel fitting hole 51a. The lens holding barrel 60 is fitted to the lens holding barrel fitting hole 51a by this insertion. Additionally, with this fitting, the housing 61 is fitted to the housing fitting hole 51b. In this fitting state, although the camera unit 19 is movable in the X direction, the rotation thereof centered on the optical axis is suppressed. In this state, the camera unit 19 is moved in the optical axis direction (X direction), and the position of the camera unit 19 in the X direction is adjusted so that the observation window 40 of the lens holding barrel 60 becomes flush with the tip surface of the tip cap 31.

Next, as illustrated in FIG. 4, if the fixing screw 71 is rotated, the fixing screw 71 enters the screw hole 77, the tip thereof hits the vertical plate portion 70b of the locking plate 70, and the locking plate 70 is pushed and moved in the Y direction. The other vertical plate portion 70b of the locking plate 70 abuts against the side wall 78 of the locking plate housing groove 51c through this movement, and the locking plate 70 is fixed within the locking plate housing groove 51c. Accordingly, positioning of the camera unit 19 in the X direction is completed. The camera unit 19 can be more firmly fixed to the tip portion main body 30 by injecting an adhesive between the locking plate 70 and the locking plate housing groove 51c from the locking plate exposure opening 80 after the completion of the positioning.

The movement of the projection 73 in the X direction is regulated by the engagement between the projection 73 of the camera unit 19 and the elongated hole 72. Therefore, since the movement of the camera unit 19 in the X direction is regulated, and the lens holding barrel 60 is fitted to and held by the lens holding barrel fitting hole 51a, the movement of the camera unit in the Y direction and in the Z direction is regulated. Accordingly, the camera unit 19 is fixed to the tip portion main body 30 without moving in the X-axis direction, the Y-axis direction, and the Z-axis direction.

The positioning and subsequent fixation of the camera unit 19 with respect to the tip portion main body 30 are simply possible by rotating the fixing screw 71 and fixing the locking plate 70 in a state where the observation window 40 of the camera unit 19 and the tip surface of the tip cap 31 coincide with each other and become flush with each other. After the fixation of the locking plate 70 by the fixing screw 71, an adhesive is put into the lens holding barrel fitting hole 51a, and thereby the camera unit 19 is anchored to the lens holding barrel fitting hole with the adhesive. In addition, the positioning of the camera unit 19 with respect to the tip portion main body 30 may be performed, for example, by making a housing tip surface abut against the tip surface of the housing fitting hole 51b instead of fine adjustment for positioning.

In the present embodiment, the vertical plate portion 70b and the rail portions 75 that guide the vertical plate portion 70b can be disposed in the spaces chamfered at the inclination surfaces 62a by chamfering the prism holding frame 62 that faces the vertical plate portion 70b of the locking plate 70 and forming the inclination surfaces 62a. Therefore, the locking plate 70 and the locking plate housing groove 51c can be made that much smaller, the locking plate and locking plate housing groove can be compactly put together, and the diameter of the tip portion 16a can be made smaller.

Second Embodiment

Figure 10:
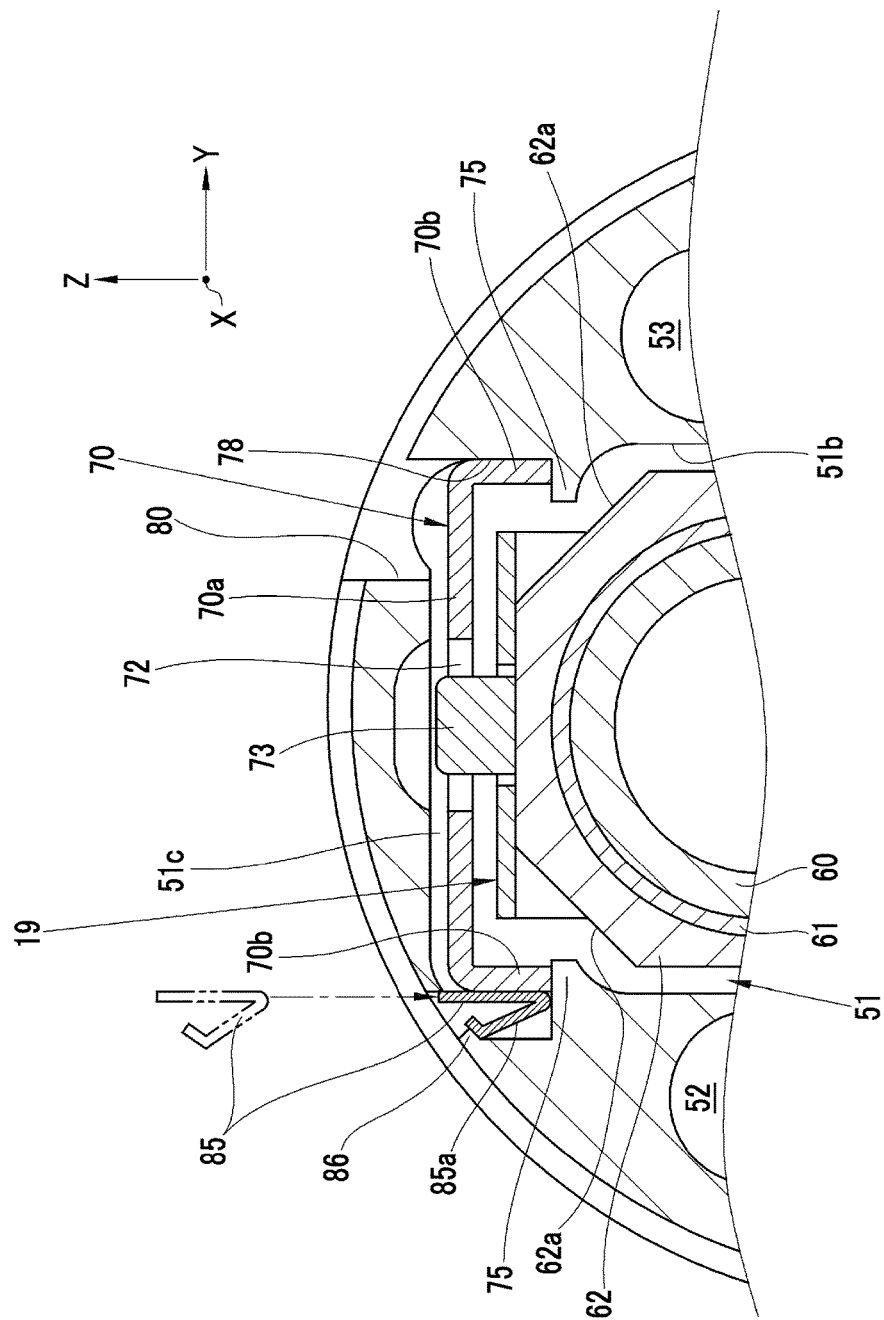
FIG. 10 is a cross-sectional view, equivalent to line IV-IV of FIG. 2, illustrating attachment of a camera unit in a second embodiment using a wedge member instead of a fixing screw.

In the above first embodiment, the locking plate 70 is pushed to one side and fixed within the housing fitting hole 51b using the fixing screw 71. However, as in a second embodiment illustrated in FIG. 10, the locking plate 70 may be pushed to one side within the locking plate housing groove 51c, using a wedge member 85 instead of the fixing screw 71. In this case, the wedge member 85 is inserted from a direction orthogonal to the insertion direction of the fixing screw 71, and the locking plate 70 is pushed against one side wall 78 of the locking plate housing groove 51c, using an inclined surface 85a of the wedge member 85.

An insertion path for the wedge member 85 is provided with a dropping regulating projection 86 that regulates dropping of the wedge member 85, and the wedge member 85 is inserted so as to ride over the dropping regulating projection 86. It is sufficient if the wedge member 85 has the inclined surface 85a and is able to shift the locking plate 70 in the Y direction, and although materials are not particularly limited, it is preferable to configure the wedge member 85 using a spring plate. In this case, when the camera unit 19 is removed from the tip portion main body 30 in the case of maintenance or repair, the removal can be simply performed by inserting a driver or the like against the spring biasing of the wedge member 85, and releasing the locking of the dropping regulating projection 86 and the wedge member 85.

Third Embodiment

Figure 11:
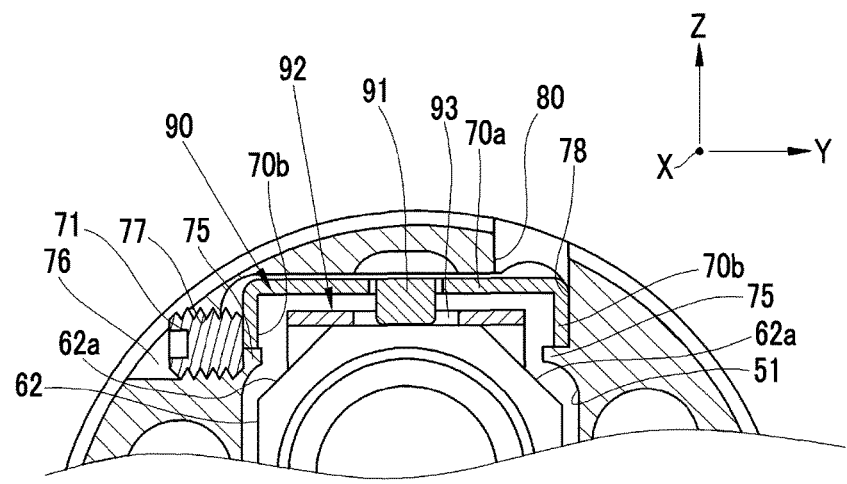
FIG. 11 is a cross-sectional view illustrating a locking plate and a reinforcing plate of a third embodiment in which the locking plate is formed with a projection and the camera unit is formed with an elongated hole.

In the above first embodiment, the elongated hole 72 is formed in the locking plate 70 and the projection 73 is formed on the camera unit 19 side. As in a third embodiment illustrated in FIG. 11, a projection 91 may be formed on the locking plate 90, and an elongated hole 93 may be formed in, for example, a reinforcing plate 92 of the camera unit 19.

Figure 12:
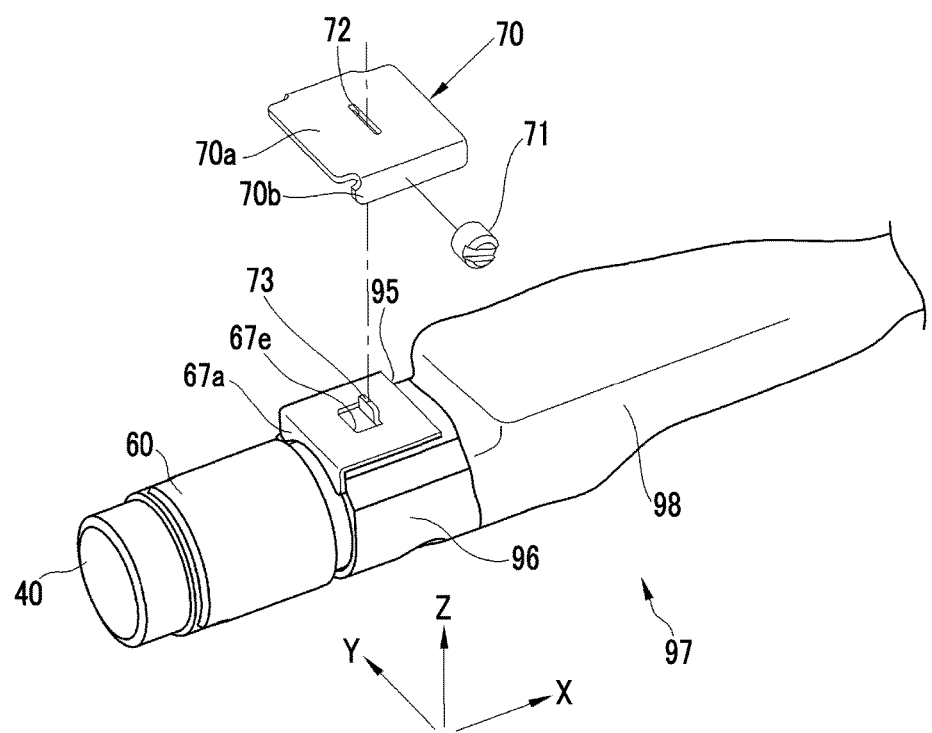
FIG. 12 is a perspective view illustrating a camera unit and a locking plate of a fourth embodiment using a fixing plate instead of the reinforcing plate.

In the above first to third embodiments, plate-like reinforcing plates 67 and 92 obtained by bending metal plates are used. However, instead of these, a base-end-side portion of the reinforcing plate main body 67c excluding the portions of the imaging element 64 that protrude to both sides may be used as a reinforcing frame that is formed so as to have a U-shaped cross-section like the signal cable coupling portion 67d. Additionally, as in a fourth embodiment illustrated in FIG. 12, the invention may be carried out with respect to a camera unit 97 reinforced by filling the inside of a protective tube 98 with a sealing agent instead of the reinforcing frame.

Fourth Embodiment

In the above first to third embodiments, the reinforcing plate 67 is formed with the projections 73 and 91, or the elongated holes 72 and 93 serving as the sliding portions. However, instead of the reinforcing plates 67 and 92, as in a fourth embodiment illustrated in FIG. 12, the camera unit 97 may be fixed to the tip portion main body 30 by providing a fixing plate 95 having the locking claw 67a and fixing the fixing plate 95 to a lens holding frame 96. In this case, similar to the respective above embodiments, the camera unit 97 is fixed to the camera unit attachment hole 51, using the locking plate 70 and the fixing screw 71 (or the wedge member 85 instead of the fixing screw 71). The camera unit 97 is covered with the protective tube 98, and has the imaging element, a circuit board, or the like built therein. In addition, the same constituent members as those of the above embodiments will be described by the same reference numerals, and duplicate description will be omitted.

In the fourth embodiment, the camera unit 97 that does not have a variable power mechanism and the reinforcing plate has been described as an example. However, even with respect to a camera unit having one or both of the variable power mechanism and the reinforcing plate, the camera unit can be similarly fixed to the tip portion main body using the fixing plate 95, the locking plate 70, the fixing screw 71, or the wedge member 85. In addition, in the camera unit 97 of the fourth embodiment, a prism of the imaging optical system may be provided or may not be provided. Additionally, the reinforcing plate 67 of the first embodiment may be provided at the camera unit 97 of the fourth embodiment illustrated in FIG. 12 that does not have a variable power function, and the camera unit may be fixed to the camera unit attachment hole 51.

In the above respective embodiments, the projections 73 and 91 are constituted of the bending pieces. However, the projections may be constituted from engagement pins or other convex members. Additionally, in the above embodiments, the elongated holes 72 and 93 are constituted of the sliding portions. However, groove portions or other guide members may be used as the sliding portions instead of the elongated holes 72 and 93. In this case, the groove portions or the other guide members allow the projections consisting of the bending pieces, the engaging pins, or the other convex members to be slidable in the Y direction, and regulate the movement of the projections in the X direction.

What is claimed is:

1. An endoscope comprising:
   a tip portion main body that is provided at a tip portion of an insertion section that is to be inserted into an inside of a body;

a camera unit attachment hole that is provided so as to penetrate the tip portion main body in an axial direction of the insertion section;

a camera unit of which tip portion is fitted into a tip portion of the camera unit attachment hole, in a state where the camera unit is inserted into the camera unit attachment hole;

a locking member that is disposed at an outer peripheral surface of the camera unit so as to be movable in a direction that is orthogonal to the axial direction, in a state where the locking member is inserted into a base end side of the camera unit attachment hole;

a projection that is provided on either one of the locking member and the camera unit;

a sliding portion that is provided on the other one of the locking member and the camera unit, the sliding portion being configured to regulate movement of the projection in the axial direction, and to enable the projection to slide in the direction that is orthogonal to the axial direction; and a locking biasing member configured to push the locking member in the direction that is orthogonal to the axial direction within the camera unit attachment hole and to push the locking member against a wall of the camera unit attachment hole, thereby fixing the locking member, in a state where the camera unit is inserted into the camera unit attachment hole.

2. The endoscope according to claim 1,
wherein the camera unit comprises a housing having a lens holding barrel at a tip thereof,
wherein the camera unit attachment hole comprises:
a lens holding barrel fitting hole to which the lens holding barrel can be fitted;
a housing fitting hole to which the housing can be fitted, the housing fitting hole being provided continuously with a base end side of the lens holding barrel fitting hole; and
a locking member housing groove in which the locking member can be housed, the locking member housing groove being provided continuously with the housing fitting hole.

3. The endoscope according to claim 2,
wherein the camera unit comprises:
a prism;
a prism holding frame that holds the prism, wherein the prism and the prism holding frame is provided continuously with the lens holding barrel; and
an attachment plate portion that is fixed to the prism holding frame and has the projection or the sliding portion.

4. The endoscope according to claim 3,
wherein the camera unit comprises a reinforcing member of which base end is fixed to a signal cable and of which tip is fixed to the prism holding frame, the reinforcing member protecting built-in elements provided between the prism holding frame and the signal cable, and
wherein the attachment plate portion is formed integrally with the reinforcing member.

5. The endoscope according to claim 4,
wherein the projection is provided on the attachment plate portion, and
wherein the sliding portion is a groove or an elongated hole, which are long in the direction orthogonal to the axial direction, the sliding portion being provided in the locking member.

6. The endoscope according to claim 2,
wherein the locking member is a locking plate that is bent at both side edges thereof, and
wherein the locking member housing groove has rail portions that guide both of the side edges in the axial direction.

7. The endoscope according to claim 3,
wherein the locking member is a locking plate that is bent at both side edges thereof, and
wherein the locking member housing groove has rail portions that guide both of the side edges in the axial direction.

8. The endoscope according to claim 4,
wherein the locking member is a locking plate that is bent at both side edges thereof, and
wherein the locking member housing groove has rail portions that guide both of the side edges in the axial direction.

9. The endoscope according to claim 5,
wherein the locking member is a locking plate that is bent at both side edges thereof, and
wherein the locking member housing groove has rail portions that guide both of the side edges in the axial direction.

10. The endoscope according to claim 6,
wherein regions of the camera unit that face both of the side edges have inclination surfaces, and the rail portions are formed in proximity to the inclination surfaces.

11. The endoscope according to claim 7,
wherein regions of the camera unit that face both of the side edges have inclination surfaces, and the rail portions are formed in proximity to the inclination surfaces.

12. The endoscope according to claim 8,
wherein regions of the camera unit that face both of the side edges have inclination surfaces, and the rail portions are formed in proximity to the inclination surfaces.

13. The endoscope according to claim 9,
wherein regions of the camera unit that face both of the side edges have inclination surfaces, and the rail portions are formed in proximity to the inclination surfaces.

14. The endoscope according to claim 1,
wherein the locking biasing member is a fixing screw that is inserted from an outer peripheral surface of the tip portion main body and thereby pushes the locking member against the wall of the camera unit attachment hole.

15. The endoscope according to claim 2,
wherein the locking biasing member is a fixing screw that is inserted from an outer peripheral surface of the tip portion main body and thereby pushes the locking member against the wall of the camera unit attachment hole.

16. The endoscope according to claim 3,
wherein the locking biasing member is a fixing screw that is inserted from an outer peripheral surface of the tip portion main body and thereby pushes the locking member against the wall of the camera unit attachment hole.

17. The endoscope according to claim 1,
wherein the locking biasing member is a wedge member that is inserted from an outer peripheral surface of the tip portion main body and thereby pushes the locking member against the camera unit attachment hole.

18. The endoscope according to claim 2,
wherein the locking biasing member is a wedge member that is inserted from an outer peripheral surface of the tip portion main body and thereby pushes the locking member against the camera unit attachment hole.

19. The endoscope according to claim 1,
wherein the tip portion main body comprises a locking member exposure opening from which exposed is a side edge of the locking member that is pushed against a side wall within the camera unit attachment hole by being pushed by the locking biasing member.

20. The endoscope according to claim 2,
wherein the tip portion main body comprises a locking member exposure opening from which exposed is a side edge of the locking member that is pushed against a side wall within the camera unit attachment hole by being pushed by the locking biasing member.

21. The endoscope according to claim 1,
wherein the locking biasing member is not in contact with the camera unit.

22. The endoscope according to claim 1,
wherein a length of the projection in the direction that is orthogonal to the axial direction is shorter than a length of the sliding portion in the direction that is orthogonal to the axial direction.

23. The endoscope according to claim 1,
wherein a length of the sliding portion in the axial direction is equal to a length of the projection in the axial direction.

24. The endoscope according to claim 1,
wherein a size of the camera unit attachment hole in the direction that is orthogonal to the axial direction is greater than a size of the locking member in the direction that is orthogonal to the axial direction.

25. The endoscope according to claim 1,
wherein an adhesive is not supplied to the projection and the sliding portion.

* * * * *